United States Patent
Fuller et al.

(12) 
(10) Patent No.: US 6,500,921 B1
(45) Date of Patent: Dec. 31, 2002

(54) SCHIFF BASE REDUCTANT CO-DISPENSE PROCESS

(75) Inventors: Norman Gery Fuller, Gilbert, AZ (US); W. Travis Johnson, Chandler, AZ (US); Michael Gaskin, Gilbert, AZ (US); Peiming Zhang, Gilbert, AZ (US)

(73) Assignee: Amersham Biosciences AB, Uppsala (SE)

(*) Notice: Subject to any disclaimer, the term of this patent is extended or adjusted under 35 U.S.C. 154(b) by 27 days.

(21) Appl. No.: 09/707,823

(22) Filed: Nov. 7, 2000

(51) Int. Cl.⁷ .............. C07H 21/00; C07K 17/08; C08L 101/06
(52) U.S. Cl. ............. 530/345; 525/54.1; 525/54.2; 530/410; 530/812; 530/815; 536/23.1
(58) Field of Search .......... 435/6, 287.2, DIG. 35, 435/DIG. 36, DIG. 37, DIG. 49, 174, 175, 177, 178, 179, 180, 181; 525/54.1, 54.2; 530/345, 402, 410, 810, 812, 813, 814, 815, 816; 536/23.1

(56) References Cited

U.S. PATENT DOCUMENTS 5,677,276 A * 10/1997 Dickerson et al. .......... 514/8
5,981,734 A   11/1999 Mirzabekov et al. ...... 536/25.3

OTHER PUBLICATIONS

"Binding Specificity and Stability of Duplexes Formed By Modified Oligonucleotides with a 4096–Hexanucleotide Microarray", Edward Timofeev et al., 2626–2634 *Nucleic Acids Research*, 2001, vol. 29, No. 12.

"Synthesis of Polyacrylamides N–Substituted with PNA–Like Oligonucleotide Mimics for Molecular Diagnostic Applications", Vladimir A. Efimov et al., 4416–4426 *Nucleic Acids Research*, 1999, vol. 27, No. 22.

"Regioselective Immobilization of Short Oligonucleotides to Acrylic Copolymer Gels", Edward N. Timofeev et al., 3142–3148 *Nucleic Acids Research*, 1996, vol. 24, No. 16.

* cited by examiner

Primary Examiner—Jeffrey E. Russel
(74) Attorney, Agent, or Firm—Royal N. Ronning, Jr.

(57) ABSTRACT

This invention provides efficient methods for producing a covalent linkage having improved chemical stability between an amine-containing biomolecule and a solid support or hydrogel surface containing an aldehyde moiety.

20 Claims, 1 Drawing Sheet

SCHIFF BASE REDUCTANT CO-DISPENSE PROCESS

BACKGROUND OF THE INVENTION

1. Field of the Invention

This invention relates to the detection of molecular interactions between biological molecules. Specifically, the invention relates to methods for producing apparatus for detecting molecular interactions between probe molecules immobilized on a microarray and target molecules exposed to the microarray. The methods of the invention can be used to provide microarrays of oligonucleotides for performing nucleic acid hybridization assays to detect molecular interactions between the oligonucleotides on the microarray and nucleic acid target molecules obtained or produced from a biological sample. The invention also provides the apparatus produced using the inventive methods, and methods for performing assays using said apparatus for detecting molecular interactions between probe and target biomolecules.

2. Background of the Invention

Immobilization of DNA, RNA, peptides, and other biomolecules through chemical attachment to a solid support or within a matrix has become an important method of molecular biology and pharmacological research and clinical diagnostics. It is especially important in the manufacturing of microarray or chip-based technologies. Microarrays have numerous applications, including diagnosis of disease, drug discovery, and genetic screening, among others.

Microfabricated arrays (biochips) of oligonucleotides and nucleic acids have utility in a wide variety of applications, including DNA and RNA sequence analysis, diagnostics of genetic diseases, gene polymorphism studies, and analysis of gene expression. In the process of biochip fabrication, large numbers of probe molecules are bound to small, defined regions of a substrate. Biochip substrates can comprise a number of substances, including glass slides, silicon wafers, or polymeric hydrogels. The chemistries that may be employed to immobilize probe molecules to a biochip array are limited to those that will be compatible with a chosen substrate and further are limited to those chemistries that will permit efficient attachment of a large number of different probe molecules to a single supporting substrate surface.

Conventional methods for attaching a biomolecule to a surface involve multiple reaction steps, often requiring chemical modification of the solid support itself, or secondary substrates such as hydrogels attached to a solid support, in order to provide an appropriate chemical functionality capable forming a covalent bond with the biomolecule. The efficiency of the attachment chemistry and strength of the chemical bonds formed are critical to the fabrication and ultimate performance of the microarray.

For arrays comprising polyacrylamide or other hydrogels, the necessary attachment functionality is currently provided by chemical modification of the hydrogel itself: amide, ester, or disulfide bonds are formed between probe molecules and the polymeric constituents of the hydrogel after polymerization and crosslinking of the hydrogel. An unresolved problem with this approach is that the attachment chemistry is not optimally stable over time, especially during subsequent manufacturing steps, and under typical conditions of use, where the microarray is exposed to high temperatures, ionic solutions, and multiple wash steps. As a consequence, the number of probe molecules on the array can be depleted during use, thus reducing the performance and limiting the useful life of the array. In addition, these methods have an inherently low coupling efficiency.

An alternative method is to covalently link an amine-terminated oligonucleotide to an available aldehyde moiety in the hydrogel matrix. In this reaction scheme, the initial product of the amine-aldehyde reaction is a chemically-reversible Schiff base. In order to stablize the bond between the solid support and the oligonucleotide, however, the Schiff base must be reduced. This has conventionally been achieved using a borane-pyridine complex dissolved in chloroform. However, a major disadvantage of this method for producing a stable covalent bond between the amine nitrogen and the aldehyde carbon atom is that the reaction must be performed as a three-phase reaction (the solid support, the aqueous hydrogel, and the organic borohydride). The triphasic nature of this reaction considerably lowers the reaction rate and yield of the reduction.

There is thus a need in the art for novel biochip arrays using different means and methods for attaching and stabilizing probe molecules to substrates. In particular, there remains a need in the art for methods that more straightforwardly and efficiently provide a stable chemical bond between amine-terminal oligonucleotide and hydrogel polymers on biological microarrays.

SUMMARY OF THE INVENTION

This invention provides methods for stabilizing amine-derivatized oligonucleotides and nucleic acids to aldehyde-functionalized solid supports. In preferred embodiments, the solid support comprises a microarray as defined herein, and most preferably the microarray further comprises a hydrogel matrix. The invention provides improved methods for forming a stable amine bond between an amine-containing biomolecules, most preferably an amino-terminal oligonucleotide or nucleic acid, and an aldehyde moiety comprising the polymeric component of the hydrogel. In preferred embodiments, the invention provides improved methods involving two phases (solid and liquid) to reduce an unstable Schiff base formed by contacting a solution of the amino-terminal oligonucleotide or nucleic acid with a hydrogel comprising an aldehyde moiety. In preferred embodiments, sodium cyanoborohydride is used to reduce the Schiff base. Microarrays produced using the methods of the invention and methods of use thereof are also provided.

Sodium cyanoborohydride is advantageously used to reduce the unstable Schiff base because this reagent is soluble in aqueous solutions and it is more effective than reductants known in the prior art. The methods provided by the invention are dramatically increased in reaction rate and yield of the stable amine adduct. In addition, sodium cyanoborohydride can be dispensed simultaneously with DNA oligonucleotides because of its aqueous solubility, does not adversely affect oligonucleotide integrity, or interfere with reaction of the terminal amine with the bound aldehyde. These features eliminate the requirement for performing a separate reduction step, which is not only time consuming but also hazardous. Further, these features facilitate automation of microarray manufacturing.

Specific preferred embodiments of the present invention will become evident from the following more detailed description of certain preferred embodiments and the claims.

DETAILED DESCRIPTION OF THE PREFERRED EMBODIMENTS

Figure 1:
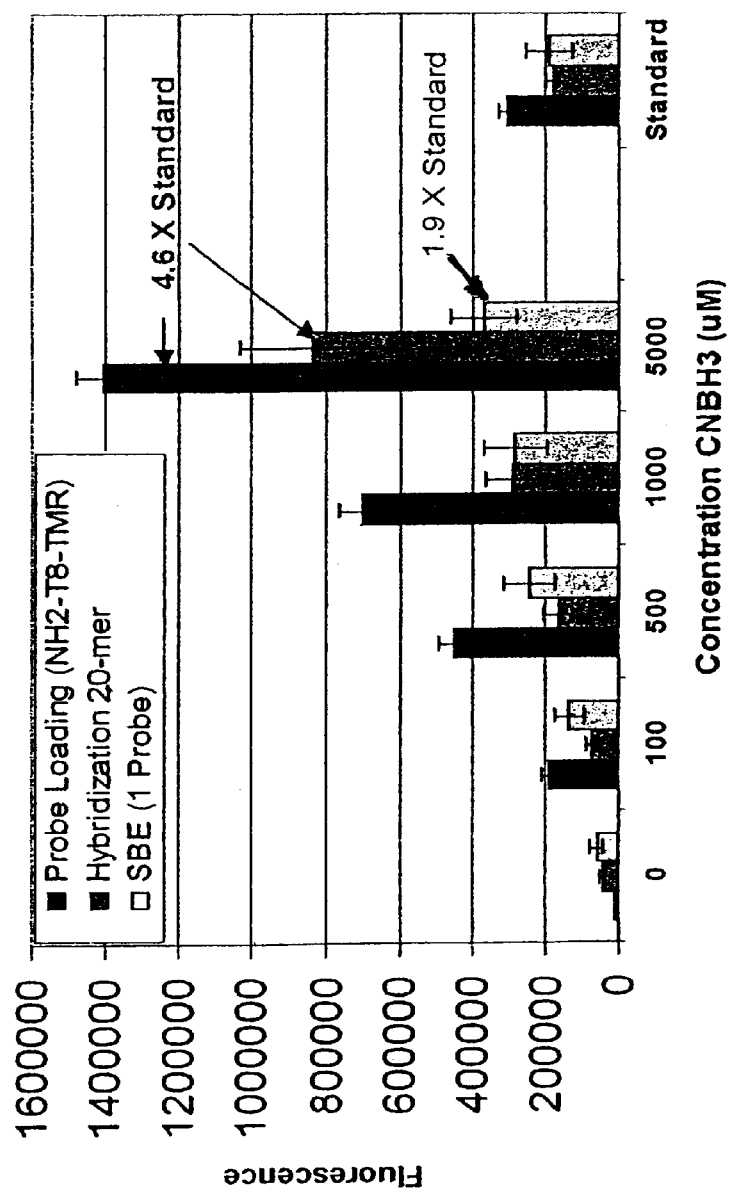
FIG. 1 is a graph showing a comparison between DNA microarrays produced using prior art borane-pyridine complex as the reductant and DNA arrays made using the method of the invention using a co-dispensed solution of sodium cyanoborohydride ($NaCNBH_3$) as the reductant.

The invention provides methods for preparing oligonucleotide and nucleic acid microarrays for performing genetic and molecular biological assays and analyses. The methods of the invention use sodium cyanoborohydride ($NaCNBH_3$) to reduce a chemically-unstable Schiff base produced by reaction of an amine-containing biomolecules, most preferably an amino-terminal oligonucleotide or nucleic acid, and a solid substrate, most preferably a polymeric hydrogel, comprising an aldehyde moiety. Adaptation of the methods disclosed herein for immobilizing peptide or polypeptide to microarrays is within the skill of those having ordinary skill in the art. The microarrays produced using this method and methods of use thereof are also provided herein.

As used herein, the terms "probe" and "biomolecular probe" refer to a biomolecule used to detect a complementary biomolecule (referred to herein as a target molecule). Preferred probe molecules include peptides, proteins, nucleic acids, polynucleotides and oligonucleotides, comprising deoxynucleotide linkages or analogues thereof known in the art (such as, inter alia, phosphorothioates and methylphosphonates). As used herein, the term "array" refers to an ordered spatial arrangement, particularly an arrangement of immobilized biomolecular probes.

As used herein, the terms "microarray," "bioarray," "biochip" and "biochip array" refer to an ordered spatial arrangement of immobilized biomolecular probes arrayed on a solid supporting substrate. Biochips, as used in the art, encompass substrates containing arrays or microarrays, preferably ordered arrays and most preferably ordered, addressable arrays, of biological molecules that comprise one member of a biological binding pair. As used with the methods provided herein, such arrays are most preferably oligonucleotide arrays comprising a nucleotide sequence that is complementary to at least one sequence that may be or is expected to be present in a DNA preparation obtained from a biological sample.

As used herein, the term "array" refers to an ordered spatial arrangement, particularly an arrangement of immobilized biomolecular probes. As used herein, the term "addressable array" refers to an array wherein the individual elements have precisely defined x and y coordinates, so that a given element at a particular position in the array can be identified.

The invention provides a biochip array of oligonucleotides comprising a supporting substrate having one or a plurality of test sites. The supporting substrate is advantageously made from any solid material, including but not limited to glass, silicon, silicon nitride, plastic, rubber, fabric, ceramics, printed circuit board, or combinations thereof. Most preferably, the substrate further comprises a polymeric surface, most preferably a hydrogel, comprising an aldehyde moiety. The supporting substrate typically has a surface area of from about 0.01 $\mu m^2$ and 5 $cm^2$, more preferably 10,000 $\mu m^2$ containing between 1 and $1 \times 10^8$ test sites, more preferably $10^4$ test sites. As used herein, the term "test site" refers to a predefined region on a substrate to which a plurality of probes, most preferably oligonucleotide probes, are immobilized. The test site may have any convenient shape, e.g., circular, rectangular, elliptical, or wedge-shaped. In preferred embodiments, the test sites have a surface area of less than about 100 $\mu m^2$. The test sites are preferably regularly spaced to provide a uniform spacing between the test sites, and are arranged on the supporting substrate so that they are separated by a distance of from about 0.05 $\mu m$ to 0.5 mm.

The probe molecules comprising the bioarray are preferably nucleic acids, peptides or proteins. Most preferably, the probe molecules comprising the bioarray are nucleic acids, oligonucleotides, or combinations thereof. Oligonucleotide probe molecules preferably comprise from about 10 to about 100, more preferably from about 10 to about 50, and most preferably from about 15 to about 30, nucleotide residues. Nucleic acid probe molecules comprise from about 10 to about 5000 basepairs, more preferably from about 100 to about 1000 basepairs, and most preferably from about 200 to about 500 basepairs. In one preferred embodiment of the present invention, the probe molecules are aptamers (i.e., oligonucleotides capable of interacting with target molecules such as peptides). Oligonucleotide or nucleic acid probe molecules can be immobilized using techniques known to those with skill in the art, wherein said immobilization does not interfere with or inhibit the ability of the probe molecules to interact with target molecules in the sample mixture. Most preferably, as described herein, the oligonucleotides contain an amino group at the 5' or 3' terminus, wherein the amino group is capable of being covalently linked to a cognate moiety on the substrate. In these embodiments, the substrate moiety is most preferably an aldehyde moiety.

In preferred embodiments, the hydrogel surface of the substrate are composed of materials including, but not limited to, polyacrylamide gel, agarose gel, polyethylene glycol, cellulose gel, or sol gel. In preferred embodiments, the hydrogel comprises polyacrylamide gel. In alternative embodiments of the present invention, the hydrogel comprises a conjugated polymer or copolymer film. Such conjugated polymer or copolymer film can be composed of materials including, but not limited to, polypyrrole, polythiophene, polyaniline, polyfuran, polypyridine, polycarbazole, polyphenylene, poly(phenylenvinylene), polyfluorene, or polyindole, or their derivatives, copolymers, or combinations thereof. In preferred embodiments, the hydrogel comprises a neutral pyrrole matrix.

In the practice of the methods of the invention, an aldehyde-functionalized substrate, preferably a aldehyde-functionalized polymer matrix and most preferably an aldehyde-functionalized hydrogel matrix, is contacted with an amine-containing biomolecules, most preferably an amino-terminal nucleic acid in the presence of an effective amount of cyanoborohydride, for a time sufficient to reduce the unstable reaction product of the aldehyde and amine moieties to a chemically-stable amine. Effective amounts of cyanoborohydride are from about 1 mM to about 20 mM, more preferably from about 2 mM to about 10 mM, and most preferably about 5 mM, for attaching 200–500 picolitres of an amino-terminated oligonucleotide at a concentration of about 100–500 $\mu M$. Preferred reaction conditions are essentially room temperature (about 25° C.) under a humidified atmosphere (60–80% relative humidity).

The Examples that follow are illustrative of specific embodiments of the invention, and various uses thereof. These Examples are set forth for explanatory purposes only, and is not to be taken as limiting the invention.

EXAMPLE 1

In the attachment of DNA to a solid support, a solution containing amine-terminated DNA and sodium cyanoborohydride is added together to an aldehyde moiety immobilized on a solid support. The series of reactions that occur in this process is shown in Scheme 1, below.

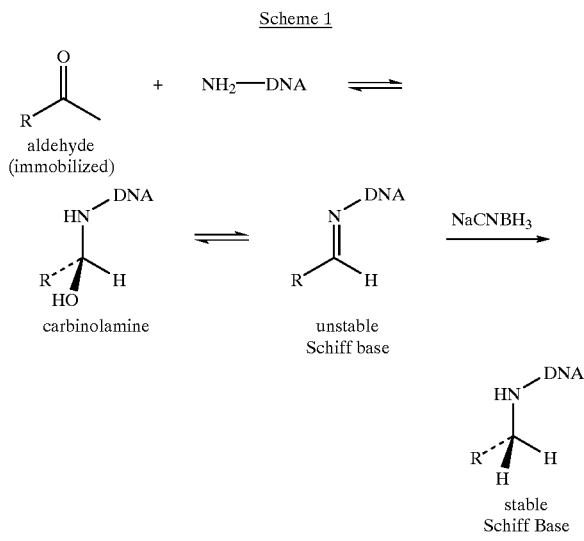

Scheme 1

In the first reaction, the amine-terminated DNA is reacted with the hydrogel-immobilized aldehydes to form carbinolamine. Next, an unstable Schiff base is formed by the reversible elimination of a water molecule. The presence of sodium cyanoborohydride reduces the unstable Schiff base, converting it into a secondary amine, driving the equilibrium of the reaction to the right and stabilizes the attachment of the DNA oligonucleotides to the solid support.

In the most preferred embodiment, the oligonucleotide and the reductant are dissolved together in 50 mM sodium phosphate buffer (pH 8); the concentration of sodium cyanoborohydride in the reaction mixture is 5 mM and the concentration of oligonucleotide is 300 $\mu$M, as determined in Example 2 below. Using piezoelectric or contact printing technology, approximately 300 to 400 picoLitres (pL) of the oligonucleotide/reductant solution is then dispensed onto a polymeric substrate composed of acrylamide, bisacrylamide, and an aldehyde comonomer moiety. This Schiff base reduction process includes a two-hour incubation at 25° C. and 80% relative humidity, to allow it to proceed to completion.

Storage tests have been performed in which amine terminated oligonucleotides were stored in the presence of 5 mM sodium cyanoborohydride at room temperature for two weeks. The storage of these solutions did not affect the attachment of the oligonucleotides to a biochip nor did it damage the oligonucleotides itself, as ascertained via oligonucleotide hybridization and single base extinction assays performed on biochips manufactured with these stored oligonucleotides.

EXAMPLE 2

Comparison of DNA Arrays Produced Using NaCNBH$_3$ as Reductant to DNA Arrays Produced Using a Conventional Reductant Results of experiments comparing sodium cyanoborohydride reduction of a Schiff base between an amino-terminal oligonucleotide and a hydrogel aldehyde with reduction using borane-pyridine in chloroform are shown in FIG. 1. The effects of inventive reduction process on microarray performance was assayed in three different ways: dye-labeled oligonucleotide loading, oligonucleotide hybridization and single-base extension assays. In all three cases, assay performance was measured by fluorescent intensity. These data show that the optimal concentration of NaCNBH$_3$ was 5 mM, as marked by the maximum fluorescence signal shown in FIG. 1. These data also show that the hybridization signal intensity was increased four fold over the hybridization signal obtained from a DNA array made using the conventional reducing agent, borane-pyridine complex in chloroform. SBE signal intensity was increased two fold over the hybridization signal obtained from a DNA array made using the conventional reducing agent.

It should be understood that the foregoing disclosure emphasizes certain specific embodiments of the invention and that all modifications or alternatives equivalent thereto are within the spirit and scope of the invention as set forth in the appended claims.

What we claim is:

1. A method for attaching a biomolecule to a solid support or to a hydrogel, the method comprising the steps of:
   (a) contacting a primary or secondary amine moiety comprising the biomolecule with an aldehyde moiety which is present in the solid support or the hydrogel, under conditions wherein a Schiff base is formed between the amine moiety and the aldehyde moiety; and
   (b) contacting the Schiff base with a solution of sodium cyanoborohydride having a concentration of from about 1 mM to about 20 mM under a relative humidity of from about 60% to about 80%.

2. The method of claim 1 wherein the solution of sodium cyanoborohydride comprises an amine-comprising biomolecule.

3. A method according to claim 1, wherein the biomolecule is an oligonucleotide.

4. A method according to claim 1, wherein the biomolecule is a DNA.

5. A method according to claim 1, wherein the biomolecule is an RNA molecule.

6. A method according to claim 1, wherein the biomolecule is a peptide.

7. A method according to claim 1, wherein the biomolecule is a protein.

8. A method according to claim 1 further comprising incubating a Schiff's base reaction mixture for about two hours at room temperature.

9. A method according to claim 8, wherein the mixture undergoes a reaction at a relative humidity of about 80%.

10. A method according to claim 1, wherein the solution of sodium cyanoborohydride has a concentration of from about 2 mM to about 10 mM.

11. A method according to claim 1, wherein the solution of sodium cyanoborohydride has a concentration of about 5 mM.

12. A method according to claim 1, wherein the biomolecule has a concentration of from about 100 $\mu$M to about 500 $\mu$M.

13. A method according to claim 1, wherein the biomolecule has a concentration of about 300 $\mu$M.

14. A method according to claim 1, wherein the biomolecule is attached to the solid support or the hydrogel at room temperature.

15. A method according to claim 1, wherein a solution comprising the biomolecule and sodium cyanoborohydride is dispensed onto the solid support or the hydrogel using piezoelectric or contact printing technology.

16. A method according to claim 1, wherein the solid support comprises a polymeric substrate.

17. A method according to claim 16, wherein the polymeric substrate comprises acrylamide, bisacrylamide, and an aldehyde comonomer moiety.

18. A method according to claim 1, wherein the biomolecule remains stable after being stored for at least two weeks in a sodium cyanoborohydride solution.

19. A method according to claim 18, wherein the sodium cyanoborohydride solution has a concentration of about 5 mM.

20. An improved method for attaching a biomolecule to a solid support or to a hydrogel in which an amine moiety comprising the biomolecule is placed in contact with an aldehyde moiety which is present in the solid support or the hydrogel under conditions wherein a Schiff base is formed between the amine moiety and the aldehyde moiety, wherein the improvement comprises contacting the Schiff base with a solution of sodium cyanoborohydride having a concentration of from about 1 mM to about 20 mM under a relative humidity of from about 60% to about 80%.

* * * * *